United States Patent [19]

McGovern et al.

[11] Patent Number: 4,530,935

[45] Date of Patent: Jul. 23, 1985

[54] INSECT REPELLENTS

[75] Inventors: Terrence P. McGovern, Bowie, Md.; Carl E. Schreck, Gainesville, Fla.

[73] Assignee: The United States of America as represented by the Secretary of Agriculture, Washington, D.C.

[21] Appl. No.: 488,530

[22] Filed: May 3, 1983

Related U.S. Application Data

[60] Continuation of Ser. No. 349,948, Feb. 18, 1982, abandoned, which is a continuation of Ser. No. 240,446, Mar. 4, 1981, abandoned, which is a division of Ser. No. 8,814, Feb. 2, 1979, Pat. No. 4,291,041.

[51] Int. Cl.$^3$ ................. C07C 103/737; A01N 37/18
[52] U.S. Cl. .................................. 514/613; 514/227; 514/255; 514/330; 514/354; 514/423; 514/623; 514/919; 564/123; 564/188
[58] Field of Search .............. 424/DIG. 10, 320; 564/123, 188

[56] References Cited

U.S. PATENT DOCUMENTS

| 2,337,846 | 12/1943 | Coleman et al. ................ 564/123 |
| 2,872,483 | 2/1959 | Bloch ........................... 424/320 X |
| 3,088,967 | 5/1963 | Paré260 ............................ 464/ |
| 3,796,803 | 3/1974 | Strong .......................... 564/188 X |
| 4,021,224 | 5/1977 | Pallos et al. ..................... 71/88 |
| 4,248,859 | 2/1981 | Rowsell et al. ................ 424/320 X |
| 4,283,420 | 8/1981 | Pigerol et al. ................. 424/320 X |

FOREIGN PATENT DOCUMENTS 1411786 10/1975 United Kingdom ................ 564/123

OTHER PUBLICATIONS

Oshima et al., CA 78:29270j, (1973).
Briel, CA 82:93905e, (1975).
Nakamura, CA 81:13291t, (1974).
McGovern et al., Mosquito News 38, 346–349, (1978).
Alexander et al., J. Econ. Entomol. 56, 58–60, (1963).
McGovern et al., Mosquito News 35, 204–210, (1975).
McGovern et al., J. Econ. Entomol., 67, 639–640, (1974).
Gouck et al., J. Econ. Entomol. 50, 175–177, (1957).
U.S. Army Environmental Hygiene Agency Reports, #5, 6, 10, 11, 12.

Primary Examiner—Thomas A. Waltz
Attorney, Agent, or Firm—M. Howard Silverstein; William E. Scott; David G. McConnell

[57] ABSTRACT

A number of novel carboxamides have been found to be useful insect repellents.

2 Claims, No Drawings

INSECT REPELLENTS

This is a continuation of Ser. No. 349,948, filed Feb. 18, 1982, now abandoned, which is a continuation of application Ser. No. 240,446, filed Mar. 4, 1981, now abandoned, which in turn is a division of Ser. No. 8,814, filed Feb. 2, 1979, now U.S. Pat. No. 4,291,041, issued Sept. 22, 1981.

BACKGROUND OF THE INVENTION

1. Field of the Invention

This invention relates to insect repellents and more particularly to certain novel carboxamides containing an alicyclic moiety and their use as insect repellents.

2. Description of the Prior Art

There is a continuing need for insect repellents or formulations thereof that are significantly more effective or longer lasting than those now in use. All of the repellents now in use for application to the skin have disadvantages, that is, they are not effective for long enough periods of time and are subject to loss by abrasion, evaporation, absorption, and immersion in water. Moreover, all cause a stinging sensation when they contact the eyelids and lips, and are effective only when they are present on the skin or clothing in relatively large quantities. Mosquitoes, sand flies, black flies, stable flies, tsetse flies, gnats, and tabanids are among the many species of biting fly that cause annoyance and distress throughout the world. Many species of biting insects spread human and animal diseases. There are many areas throughout the world in both developed and developing nations where the use of protective clothing and repellents is the only means available to individuals for personal protection. Deet(N,N-diethyl-m-toluamide) has proved to be the most outstanding all-purpose individual repellent yet developed (Proceedings of a Symposium, University of Alberta, Edmonton, Canada, May 16–18, 1972, Defense Research Board, Ottawa, Canada, 1973. DR-217: 109–113). Deet was reported as a promising repellent in 1954 (Journal of Organic Chemistry, 19, 493, 1954). Since that time, no repellent has been reported as being superior to deet as an all-purpose repellent despite a continuing search for such a chemical.

SUMMARY OF THE INVENTION

An object of this invention is to provide a class of compounds that are useful as insect repellents.

The above object is accomplished by a number of novel carboxamides having from about 11 to about 18 carbon atoms and containing an alicyclic moiety. Many of these compounds are more effective than presently available repellents and many are effective against a wide variety of insects.

DESCRIPTION OF THE INVENTION

The compounds of this invention are represented by the formula below

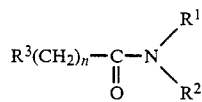

wherein $R^3$ is one of the groups A, B, or C

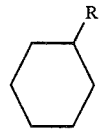 (A)

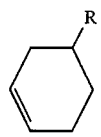 (B)

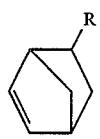 (C)

R is hydrogen or lower alkyl, n is zero or the positive integer one, two, or three, each of $R^1$ and $R^2$ is alkyl, or taken together represent an alkylene, an alkenylene, an alkyl substituted alkylene, an alkylene ether, and alkyl substituted alkylene ether, or an alkyl substituted alkylene amine ring structure.

The compounds of this invention are useful as insect repellents and are particularly effective against many Dipteran.

The novel compounds of this invention are especially effective in repelling a wide variety of insects such as ticks, chiggers, cockroaches, and biting diptera such as mosquitoes, stable flies, deer flies, black flies, and sand flies. Certain novel amides reported in this invention are about equally as effective as deet against mosquitoes and are significantly more repellent than deet against other biting flies when tested on skin. The skin test is the obvious critical test when one considers personal protection; however, clothing repellents are also very important especially in areas of heavy mosquito infestations (The Journal of the American Medical Association, 196, 253, 1966). Certain amides of this invention provide exceptional protection against mosquitoes when applied to cloth.

The amides were synthesized as follows: the appropriate acid chloride was slowly added with stirring to an anhydrous ether solution of the amine cooled in an ice bath (either the amine itself or pyridine was used as a hydrochloric acid scavenger). The reaction mixture was allowed to warm to room temperature and then allowed to stand for several hours, usually overnight. The amides were isolated by routine extraction procedures and purified by distillation under high vacuum. Purity was checked by gas chromatographic analysis.

A typical procedure is illustrated by the following description of the synthesis of 1-(3-cyclohexenecarbonyl)piperidine, compound 20 in Table 1: 3-cyclohexenecarbonyl chloride, 28.9 grams (0.2 mole), was added dropwise to an ice cold solution (0°–10° C.) of piperidine, 34 grams (0.4 mole) in 250 ml of anhydrous ether. The solution was stirred vigorously during the addition. The reaction mixture was allowed to warm to room temperature and to stand overnight. Water was added to dissolve the precipitated piperidine hydrochloride salt. The organic layer was then washed sequentially with 5% hydrochloric acid and sodium bicarbonate solutions and finally with a saturated salt solution until the wash was neutral to litmus paper and dried over anhydrous magnesium sulfate. After filtering, the solvent was removed under reduced pressure (water pump). The crude amide was distilled under high vacuum to give 31.4 grams of product—b.p. 114°-15° C./0.2 mm Hg), $n_D{}^{25}$ 1.5159.

The physical constants of the compounds are presented in Table 1.

The repellent activity of the amides of the present invention was demonstrated by practical laboratory and field tests against mosquitoes and a variety of other biting diptera. The effectiveness of the repellents was determined by directly comparing their repellency with that of deet in tests on skin and with dimethyl phthalate in tests on cloth.

In the following description of the testing procedures the first confirmed bite is defined as a bite followed by another within thirty minutes.

For the purposes of this invention, the compounds were tested as solutes in alcohol, acetone, or other volatile solvent. However, other compatible liquid or solid carriers may also be used.

TESTING PROCEDURES

Stable Flies

The repellents were applied as 1-ml aliquots of a 25% ethanol solution and spread evenly over the forearm of a subject from wrist to elbow. Since the ethanol solution was formulated on a weight-volume basis, 250 mg of repellent was applied to the forearm in each test. The most promising compounds (those equal to or better than the deet standard at the 25% dosage) were then tested as 12.5% and 6.25% ethanol solutions.

The evaluations were carried out in an outdoor cage (103 cm square and 133 cm high) constructed of aluminum and having a solid top and bottom and screen wire on four sides. Four of the sides had port openings covered with 30.5-cm (12-in.) tubular cloth stockinettes. The centers of the ports were 30 cm from the bottom of the cage, which rested on a table 80 cm high. One arm each of up to four treated subjects at a time could be inserted through the ports into the cage.

Approximately 12,000 *S. calcitrans* pupae were placed in cups and allowed to emerge in the test cage over an 8-day period. The tests were started the 4th day, when approximately 8000 flies had emerged. The remaining 4000 that emerged over the next 4 days maintained a relatively stable population in respect to numbers and avidity. Citrated beef blood on a cotton pad was offered for 45 minutes each day after the repellent tests were completed. This short-term feeding period provided a small but adequate food intake, and avidity was not reduced as a result of complete engorgement. Results obtained when an untreated forearm was inserted into the test cage before and during the tests each day gave a measure of the avidity of the flies, though it was impossible to count the attacks on the untreated arm.

The effectiveness of each chemical was determined by the protection time; that is, the time between treatment and the first confirmed bite. Therefore, 30 minutes after the application of the test chemical and every 30 minutes thereafter, the treated arms were inserted into the test cage for 3 minutes unless bites occurred sooner.

Since test subjects differ in attractiveness and insects differ in avidity, the best measure of the effectiveness of a repellent is its ratio of protection time vs. that of a standard repellent used in similar conditions. Deet was the standard in all of the tests reported here. It was paired with each of the other candidate repellents in 10 different test series.

The experimental design used was a round-robin series in which each repellent was paired concurrently against another repellent on the arms of a subject. An adjusted average protection time that allowed for individual variation between test subjects and test conditions was then computed (Soap and Chemical Specialties, 33, 115–17 and 129–133, 1957).

Black Flies

The principal test site was in the vicinity of Kidney Pond, Baxter State Park, Maine. Meadows bordered by fast moving mounting streams and an abundance of wildlife provided optimum breeding conditions in this area. Several species of blackflies were represented in the population attacking four test subjects. Of these, the two most abundant were identified as *Simulium venustum* Say and *Prosimulium mixtum* Syme and Davis. Repellents were applied as 1-ml aliquots of a 12.5 or 25% ethanol solution and spread evenly over the forearm of a subject from wrist to elbow. The ethanol solution was formulated on a weight-volume basis, so either 125 or 250 mg of repellent was applied in each test.

Treated arms were continuously exposed to the natural populations of flies. Subjects intermittently moved about with arms raised or on hips, squatted, or sat down for brief periods of 5 to 10 minutes. These positions, coupled with slow walking and standing every few minutes, appeared to be attractive to black flies (Simulids and Prosimulids) and were used as standard procedure in all tests. Head-nets and gloves were worn by the test subjects to prevent attack on exposed untreated parts of the body.

Two series of round-robin tests were conducted in the spring of 1977 using 12.5 or 25% solutions of repellent in ethanol; one series was conducted during June 1978 using a 25% solution of repellent in ethanol. The effectiveness of each chemical was determined by the protection time, i.e., the time between treatment and the first confirmed bite. Since test subjects differ in attractiveness and insects differ in avidity, the best measure of the effectiveness of a repellent is the ratio of its protection time to that of a standard repellent under similar conditions. Deet was the standard repellent in these tests.

In the round-robin test each repellent was paired with each other repellent on the arms of a subject (four or five replicates). An adjusted average protection time that allowed for individual variations between test subjects and test conditions was then computed. Black fly landing rates ranged from 14 to 40/minute during the test period.

Deer Flies

The compounds and the standard repellent, deet, were tested on the forearms of human subjects against natural populations of the deer fly, *Chrysops atlanticus*. The materials were formulated as 25% ethanol solutions and applied at the rate of 1 ml per forearm. The field tests were conducted along logging roads adjacent to the marshes of the Ogeechee River at Richmond Hill, Ga., where *C. atlanticus* populations occur in great numbers annually. Since the flies are attracted to motion, the test subjects continually walked while exposing their treated arms to the flies. The tests were terminated when a confirmed bite was received. The chemicals were evaluated in round-robin tests with five compounds and a deet standard in each series. During the 3-week test period the landing rate averaged 33 flies/man and ranged from 13 to 54/man.

Sand Flies

Two test sites were used, one at YankeeTown, Fla. on the Gulf coast and one at Parris Island, S.C. The repellents were applied as 25% solutions in ethanol on the forearms (wrist to elbow) of test subjects. Because of the limited period of insect activity (early morning or late afternoon to dusk) the subjects were pretreated 2 hours prior to the test period to effect aging of the repellents. The repellents were evaluated against the standard repellent, deet, in paired tests (3 replications). A test repellent was applied to one arm of a subject and deet to the other. Effectiveness were determined by the number of bites received during the test period. A control (no repellent treatment) was included in each test to ascertain the level of insect pressure.

Mosquitoes

Tests on skin.

For laboratory tests, 1 ml of a 25% ethanol solution of the repellent was spread evenly over the forearm of the subject. The treated forearms were exposed to about 1500 female laboratory reared *Aedes aegypti* or *Anopheles quadrimaculatus* mosquitoes in cages. Effectiveness was based on complete protection, that is, the time between treatment and the first confirmed bite. The effectiveness of the compounds was compared to that of the standard repellent, deet. The chemicals were tested in a round-robin series in a balanced incomplete block design in which each repellent in the series was paired against each other repellent in the series on opposite arms of a given number of subjects.

The field tests were conducted at sites adjacent to Mosquito Lagoon near New Smyrna Beach, Fla. The repellents were applied in the same manner as for the laboratory tests. The treated arms were exposed continuously to the natural population of mosquitoes until the first confirmed bite was received. Protection clothing and head nets were worn by the test subjects to protect against attack on exposed untreated parts of the body. The experimental design used was a balanced incomplete block as in the laboratory tests.

Tests on cloth.

Test materials were applied at the rate of 3.3 g of compound per 0.1 m$^2$ cloth to a measured portion (0.03 m$^2$) of a cotton stocking as 10% solutions in acetone or other volatile solvent. After 2 hours, the treated stocking was placed over an untreated nylon stocking on the arm of a human subject and exposed for 1 minute in a cage containing about 1500 five- to eight-day old *A. aegypti* or *A. quadrimaculatus*. The test exposure was repeated at 24 hours and then at weekly intervals until five bites were received in 1 minute. Days to the first bite and to five bites were recorded. Between tests, the treated stockings were placed on a rack at room temperature, and evaporation was allowed to continue. A standard repellent, dimethyl phthalate, was tested concurrently and was effective for 11 to 21 days against both mosquito species.

The merits of the present invention are illustrated in the results shown in the tables.

The data in Table 2 show compounds 2, 7, 20, 33, 34, 47, and 49 were more active against the stable fly than the deet standard at all concentrations tested. Compounds 20 and 34 were significantly more effective than deet at all three dosages (0.05% level of confidence). Compounds 21 and 35 were more active than deet at two concentrations and equal to it at the lowest concentration tested. The repellent effect of certain of these chemicals was as much as 4.5× that of deet and provided protection up to 9 hours; the protection time of deet ranged from 2 to 3 hours. Data for compounds 4, 6, 17, 18, 19, 31, and 45 are shown to illustrate the unpredictability of repellent activity of closely related chemicals.

The data in Table 3 show all eight compounds and deet are very good black fly repellents. Compound 21 is significantly more effective than deet at the 25% dosage providing about 10.5 hours protection. There is no significant difference between the remaining compounds and deet at the 25% dosage. Although not significantly more effective than deet, the adjusted mean for compound 20 was 0.5 and 1.5 hours greater than that of deet at the two test dosages. Compounds 7 and 35 provided about 7 hours protection; compounds 20 and 47 provided over 8 hours protection; compounds 6 and 33 provided about 9 hours protection.

The data in Table 4 show 10 compounds that exceeded deet in repellency against deer flies. Compound 20 was significantly more effective than deet with an adjusted mean protection time of 6.3 hours.

The data in Table 5 show compounds 2, 7, 20, and 35 greatly superior to deet in tests conducted in Florida against the sand fly *Culicoides mississippiensis*. Compounds 2 and 20 were also superior to deet in the Parris Island tests against *Culicoides hollensis*. Deet is considered a good repellent for sand flies (Meditsinskaya Parazitologiya i Parazitarnye Bolezni, 35 (5), 549, 1963). A biting rate of about 5/hour would make the presence of sand flies tolerable to most people (Journal of Economic Entomology, 64 (1), 264, 1971). The data show certain compounds of this invention equalling or exceeding this criteria in one test and equalling or closely approaching it in the second test. The number of bites experienced by the check, clearly shows very high insect pressure during these tests, emphasizing the effectiveness of the repellents.

The data in Table 6 show the relative repellency of compounds of this invention against mosquitoes when applied to skin in laboratory and field tests. Deet is an excellent mosquito repellent (The Journal of the American Medical Association, 196, 253, 1966). Repellents 33 and 34 were about equally as effective against *Aedes aegypti* as deet; repellents 19, 20, 21, and 34 were about equally as effective against *Anopheles quadrimaculatus* as deet. In field tests, repellents 2 and 20 were 1.5 and 1.4 times as effective as deet against *Aedes taeniorhynchus* and 4, 6, 7, 21, 33, and 47 were about equally as effective as deet. Because deet is such an effective mosquito repellent, chemicals having 0.5 ratios to deet are considered good mosquito repellents.

The data in Table 7 show 91 of the repellents were more effective than the standard against one species of mosquito and 9 other compounds were about equally as effective as the standard. Repellents 91, 100, 101, and 115 provided outstanding protection of over 200 days and 29 other repellents provided exceptional protection of over 100 days against one species or the other. All chemicals providing 11 or more days protection are considered promising repellents.

The foregoing examples of repellent action of these novel amides against specific insect pests is meant to be illustrative rather than limiting. For example, the compounds of the present invention can be mixed with inert ingredients or with other known insect repellents. The compounds may also be formulated or embodied into repellent compositions in the form of creams, lotions, emulsions, suspensions, solutions, dusts, and aerosol or other type of sprays.

Although insect repellents are usually applied to the skin, the compounds of this invention and formulations containing them are also useful when applied to clothing, netting, packaging, shipping containers, animals, and growing plants.

TABLE 1

Physical constants of compounds synthesized in accordance with the procedures of this invention $-N\begin{matrix}R^1\\R^2\end{matrix}$

| No. | R¹/R² | B.p. (°C./mmHg) or m.p. (°C.) | $n_D^{25}$ |
|---|---|---|---|

| 1 | N,N—Dimethylamino | 69–70/0.45 | 1.4794 |
| 2 | N,N—Dipropylamino | 93–5/0.45 | 1.4685 |
| 3 | N,N—Dibutylamino | 133/1.5 | 1.4675 |
| 4 | 1-Pyrrolidyl | 67–8 | |
| 5 | 1-Piperidyl | 108/0.45 | 1.5030 |
| 6 | 1-Hexahydro-1H—azepinyl | 120/0.25 | 1.5038 |
| 7 | 2-Methyl-1-piperidyl | 110–13/0.7 | 1.5001 |
| 8 | 3-Methyl-1-piperidyl | 114–16/0.45 | 1.4974 |
| 9 | 4-Methyl-1-piperidyl | 113–14/0.8 | 1.4970 |
| 10 | 2-Ethyl-1-piperidyl | 131/1.5 | 1.4970 |
| 11 | 2,6-Dimethyl-1-piperidyl | 109–11/0.5 | 1.4950 |
| 12 | 1,2,3,6-Tetrahydro-1-pyridinyl | 107–9/0.5 | 1.5175 |
| 13 | 4-Methyl-1-piperazinyl | 100–2/0.1 | 1.5041 |
| 14 | 4-Morpholinyl | 57–8 | |
| 15 | 2,6-Dimethyl-4-morpholinyl | 116–17/0.3 | 1.4919 |

(cyclohexenyl-C(O)-NR¹R²)

| 16 | N,N—Dimethylamino | 75–6/0.4 | 1.4960 |
| 17 | N,N—Dipropylamino | 88/0.15 | 1.4804 |
| 18 | N,N—Dibutylamino | 103/0.1 | 1.4775 |
| 19 | 1-Pyrrolidyl | 44–5 | |
| 20 | 1-Piperidyl | 114–15/0.2 | 1.5159 |
| 21 | 1-Hexahydro-1H—azepinyl | 105–6/0.15 | 1.5151 |
| 22 | 2-Methyl-1-piperidyl | 110–12/0.1 | 1.5106 |
| 23 | 3-Methyl-1-piperidyl | 108–10/0.1 | 1.5087 |
| 24 | 4-Methyl-1-piperidyl | 110–12/0.15 | 1.5087 |
| 25 | 2-Ethyl-1-piperidyl | 114–15/0.1 | 1.5068 |
| 26 | 2,6-Dimethyl-1-piperidyl | 112–13/0.1 | 1.5055 |
| 27 | 1,2,3,6-Tetrahydro-1-pyridinyl | 114–16/0.45 | 1.5315 |
| 28 | 4-Methyl-1-piperazinyl | 112–14/0.1 | 1.5181 |
| 29 | 4-Morpholinyl | 114–16/0.25 | 1.5194 |
| 30 | 2,6-Dimethyl-4-morpholinyl | 115–16/0.4 | 1.5043 |

(2-methylcyclohexyl-C(O)-NR¹R²)

| 31 | N,N—Dipropylamino | 100/0.7 | 1.4682 |
| 32 | N,N—Dibutylamino | 126/0.9 | 1.4669 |
| 33 | 1-Pyrrolidyl | 95/0.25 | 1.4941 |
| 34 | 1-Piperidyl | 104–6/0.5 | 1.4970 |
| 35 | 1-Hexahydro-1H—azepinyl | 115–18/0.9 | 1.5000 |
| 36 | 2-Methyl-1-piperidyl | 141–3/0.25 | 1.4930 |
| 37 | 3-Methyl-1-piperidyl | 168–70/18 | 1.4909 |
| 38 | 4-Methyl-1-piperidyl | 108/0.8 | 1.4908 |

TABLE 1-continued

Physical constants of compounds synthesized in accordance with the procedures of this invention

| No. | R¹/R² | B.p. (°C./mmHg) or m.p. (°C.) | $n_D^{25}$ |
|---|---|---|---|
| 39 | 2-Ethyl-1-piperidyl | 175–8/18 | 1.4930 |
| 40 | 2,6-Dimethyl-1-piperidyl | 108–10/0.5 | 1.4905 |
| 41 | 1,2,3,6-Tetrahydro-1-pyridinyl | 118–20/1.3 | 1.5100 |
| 42 | 4-Methyl-1-piperazinyl | 120–2/1.0 | 1.4990 |
| 43 | 4-Morpholinyl | 108–9/0.4 | 1.4975 |
| 44 | 2,6-Dimethyl-4-morpholinyl | 75–7 | |

(2-methylcyclohexenyl-C(O)-NR¹R²)

| 45 | N,N—Dipropylamino | 108/2.0 | 1.4794 |
| 46 | N,N—Dibutylamino | 120/0.45 | 1.4765 |
| 47 | 1-Pyrrolidyl | 133–6/0.2 | 1.5082 |
| 48 | 1-Piperidyl | 109/0.5 | 1.5090 |
| 49 | 1-Hexahydro-1H—azepinyl | 135/0.9 | 1.5116 |
| 50 | 2-Methyl-1-piperidyl | 120–2/1.1 | 1.5049 |
| 51 | 3-Methyl-1-piperidyl | 120–2/1.3 | 1.5035 |
| 52 | 4-Methyl-1-piperidyl | 122–4/1.0 | 1.5020 |
| 53 | 2-Ethyl-1-piperidyl | 116–18/0.5 | 1.5036 |
| 54 | 2,6-Dimethyl-1-piperidyl | 115–17/0.5 | 1.5017 |
| 55 | 1,2,3,6-Tetrahydro-1-pyridinyl | 113–15/0.7 | 1.5234 |
| 56 | 4-Methyl-1-piperazinyl | 105–7/0.3 | 1.5106 |
| 57 | 4-Morpholinyl | 104–5/0.2 | 1.5115 |
| 58 | 2,6-Dimethyl-4-morpholinyl | 122–5/0.4 | 1.4990 |

(bicyclic-C(O)-NR¹R²)

| 59 | N,N—Dipropylamino | 93–5/0.2 | 1.4900 |
| 60 | N,N—Dibutylamino | 100–2/0.1 | 1.4862 |
| 61 | 1-Pyrrolidyl | 105–8/0.15 | 1.5262 |
| 62 | 1-Piperidyl | 111–13/0.2 | 1.5244 |
| 63 | 1-Hexahydro-1H—azepinyl | 121–2/0.4 | 1.5262 |
| 64 | 2-Methyl-1-piperidyl | 108–9/0.2 | 1.5197 |
| 65 | 3-Methyl-1-piperidyl | 110–12/0.3 | 1.5169 |
| 66 | 4-Methyl-1-piperidyl | 98–100/0.1 | 1.5163 |
| 67 | 2-Ethyl-1-piperidyl | 108–9/0.15 | 1.5168 |
| 68 | 2,6-Dimethyl-1-piperidyl | 100–1/0.15 | 1.5166 |
| 69 | 1,2,3,6-Tetrahydro-1-pyridinyl | 110/0.1 | 1.5401 |
| 70 | 4-Methyl-1-piperazinyl | 103–4/0.1 | 1.5253 |
| 71 | 4-Morpholinyl | 99–100/0.1 | 1.5258 |
| 72 | 2,6-Dimethyl-4-morpholinyl | 100–2/0.1 | 1.5113 |

(cyclohexyl-CH₂C(O)-NR¹R²)

| 73 | N,N—Dimethylamino | 87–8/0.45 | 1.4780 |
| 74 | N,N—Dipropylamino | 108–9/0.45 | 1.4708 |
| 75 | N,N—Dibutylamino | 139/0.75 | 1.4698 |
| 76 | 1-Pyrrolidyl | 110–12/0.25 | 1.4977 |
| 77 | 1-Piperidyl | 109–11/0.2 | 1.5000 |
| 78 | 1-Hexahydro-1H—azepinyl | 114–16/0.2 | 1.5019 |
| 79 | 2-Methyl-1-piperidyl | 105–7/0.2 | 1.4945 |
| 80 | 3-Methyl-1-piperidyl | 118/0.4 | 1.4942 |
| 81 | 4-Methyl-1-piperidyl | 121/0.5 | 1.4935 |
| 82 | 2-Ethyl-1-piperidyl | 122–4/0.2 | 1.4943 |
| 83 | 2,6-Dimethyl-1-piperidyl | 121–3/0.3 | 1.4942 |
| 84 | 1,2,3,6-Tetrahydro-1-pyridinyl | 122–4/0.15 | 1.5114 |
| 85 | 4-Methyl-1-piperazinyl | 109/0.15 | 1.5016 |
| 86 | 4-Morpholinyl | 68–70 | |

TABLE 1-continued

Physical constants of compounds synthesized in accordance with the procedures of this invention

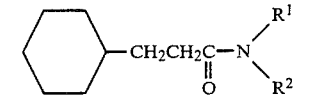

| No. | $-N\begin{matrix}R^1\\R^2\end{matrix}$ | Physical constants B.p. (°C./mmHg) or m.p. (°C.) | $n_D^{25}$ |
|---|---|---|---|
| 87 | 2,6-Dimethyl-4-morpholinyl | 125–7/0.5 | 1.4892 |

| No. | | B.p. | $n_D^{25}$ |
|---|---|---|---|
| 88 | N,N—Dimethylamino | 100–2/0.4 | 1.4782 |
| 89 | N,N—Dipropylamino | 117–18/0.45 | 1.4715 |
| 90 | N,N—Dibutylamino | 133–5/0.4 | 1.4701 |
| 91 | 1-Pyrrolidyl | 126–7/0.2 | 1.4928 |
| 92 | 1-Piperidyl | 129–31/0.2 | 1.4950 |
| 93 | 1-Hexahydro-1H—azepinyl | 131–4/0.3 | 1.4985 |
| 94 | 2-Methyl-1-piperidyl | 128–30/0.35 | 1.4933 |
| 95 | 3-Methyl-1-piperidyl | 136–8/0.5 | 1.4912 |
| 96 | 4-Methyl-1-piperidyl | 136–7/0.5 | 1.4919 |
| 97 | 2-Ethyl-1-piperidyl | 126–7/0.1 | 1.4938 |
| 98 | 2,6-Dimethyl-1-piperidyl | 135/0.35 | 1.4895 |
| 99 | 1,2,3,6-Tetrahydro-1-pyridinyl | 134–5/0.5 | 1.5070 |
| 100 | 4-Methyl-1-piperazinyl | 139–40/0.1 | 1.4966 |
| 101 | 4-Morpholinyl | 122–4/0.1 | 1.4961 |
| 102 | 2,6-Dimethyl-4-morpholinyl | 123–5/0.1 | 1.4876 |

| 103 | N,N—Dimethylamino | 109–10/0.4 | 1.4764 |
|---|---|---|---|
| 104 | N,N—Dipropylamino | 128–30/0.4 | 1.4712 |
| 105 | N,N—Dibutylamino | 148/0.4 | 1.4705 |
| 106 | 1-Pyrrolidyl | 137–9/0.4 | 1.4905 |
| 107 | 1-Piperidyl | 139–40/0.5 | 1.4920 |
| 108 | 1-Hexahydro-1H—azepinyl | 153–4/0.5 | 1.4940 |
| 109 | 2-Methyl-1-piperidyl | 142–3/0.45 | 1.4909 |
| 110 | 3-Methyl-1-piperidyl | 143–5/0.5 | 1.4882 |
| 111 | 4-Methyl-1-piperidyl | 145–7/0.45 | 1.4875 |
| 112 | 2-Ethyl-1-piperidyl | 145/0.25 | 1.4910 |
| 113 | 2,6-Dimethyl-1-piperidyl | 151–3/0.5 | 1.4874 |
| 114 | 1,2,3,6-Tetrahydro-1-pyridinyl | 145–6/0.45 | 1.5035 |
| 115 | 4-Methyl-1-piperazinyl | 134–5/0.15 | 1.4975 |
| 116 | 4-Morpholinyl | 149–51/0.45 | 1.4932 |
| 117 | 2,6-Dimethyl-4-morpholinyl | 145–7/0.45 | 1.4828 |

TABLE 2

Repellency of compounds to the stable fly *Stomoxyx calcitrans* when applied to the skin at various concentrations in ethanol and compared to deet as a test standard

| No. | % Conc. | Protection time (minutes) Range | Adjusted mean | Ratio to deet[a] | No. of tests |
|---|---|---|---|---|---|
| 2 | 6.25 | 30–90 | 55 | 1.7 | 3 |
|  | 12.5 | 300–360 | 315 | 4.50[b] | 5 |
|  | 25.0 | 210–463 | 321 | 2.02[b] | 5 |
| 4 | 25.0 | 30–270 | 103 | 0.4 | 5 |
| 6 | 25.0 | 30–268 | 183 | 0.71 | 5 |
| 7 | 25.0 | 120–300 | 246 | 2.01[b] | 4 |
| 17 | 25.0 | 180–360 | 225 | 0.85 | 5 |
| 18 | 25.0 | 30–189 | 122 | 0.46 | 5 |
| 19 | 25.0 | 90–420 | 237 | 1.0 | 5 |
| 20 | 6.25 | 30–120 | 103 | 2.5[b] | 3 |
|  | 12.5 | 60–240 | 128 | 2.4[b] | 4 |
|  | 25.0 | 360–390 | 387 | 2.39 | 5 |
| 21 | 6.25 | 30–60 | 33 | 1.0 | 5 |
|  | 12.5 | 270–450 | 306 | 1.42 | 5 |
|  | 25.0 | 300–510 | 457 | 3.78[b] | 4 |
| 31 | 25.0 | 30–60 | 36 | 0.2 | 5 |

TABLE 2-continued

Repellency of compounds to the stable fly *Stomoxyx calcitrans* when applied to the skin at various concentrations in ethanol and compared to deet as a test standard

| No. | % Conc. | Protection time (minutes) Range | Adjusted mean | Ratio to deet[a] | No. of tests |
|---|---|---|---|---|---|
| 33 | 6.25 | 60–180 | 80 | 1.6 | 3 |
|  | 12.5 | 90–210 | 150 | 3.3[b] | 4 |
|  | 25.0 | 240–270 | 266 | 1.6 | 4 |
| 34 | 6.25 | 30–120 | 118 | 2.4[b] | 3 |
|  | 12.5 | 270–330 | 320 | 4.57[b] | 5 |
|  | 25.0 | 390–510 | 419 | 2.6[b] | 4 |
| 35 | 6.25 | 30–30 | 30 | 1.0 | 5 |
|  | 12.5 | 210–375 | 326 | 3.27[b] | 5 |
|  | 25.0 | 390–510 | 459 | 2.9[b] | 4 |
| 36 | 25.0 | 30–120 | 101 | 1.43 | 5 |
| 45 | 25.0 | 30–180 | 78 | 0.44 | 5 |
| 47 | 6.25 | 30–90 | 63 | 1.9 | 3 |
|  | 12.5 | 120–270 | 230 | 3.29[b] | 5 |
|  | 25.0 | 150–405 | 264 | 1.66 | 5 |
| 49 | 6.25 | 30–60 | 38 | 1.15 | 5 |
|  | 12.5 | 150–330 | 306 | 1.42 | 5 |
|  | 25.0 | 480–510 | 538 | 3.02[b] | 5 |
| 50 | 25.0 | 60–150 | 125 | 1.41 | 5 |

[a]Data compiled from a number of different tests, accounting for the fluctuation between protection time and ratio to deet among the members of the series.
[b]Significantly different from deet at the 0.05% level of confidence.

TABLE 3

Repellency of compounds applied to the skin as 12.5 and/or 25% ethanol solutions compared with deet against blackflies in two series of field tests

| No. | % Conc. | Protection time (min) Range | Adjusted mean | Ratio to deet | No. of tests |
|---|---|---|---|---|---|
| *Test I (1977)* | | | | | |
| Deet (Std) | 12.5 | 145–283 | 161 | 1.00 | 5 |
|  | 25.0 | 287–511 | 426 | 1.00 | 4 |
| 20 | 12.5 | 123–314 | 193 | 1.20[a] | 5 |
|  | 25.0 | 413–565 | 505 | 1.19[a] | 4 |
| 7 | 12.5 | 26–222 | 95 | 0.59 | 5 |
|  | 25.0 | 309–515 | 424 | 1.00[a] | 4 |
| 35 | 12.5 | 24–126 | 93 | 0.58 | 5 |
|  | 25.0 | 342–542 | 412 | 0.97[a] | 4 |
| 2 | 12.5 | 25–112 | 71 | 0.44 | 5 |
|  | 25.0 | 198–375 | 314 | 0.74[a] | 4 |
| *Test II (1978)* | | | | | |
| Deet (Std) | 25.0 | 399–623 | 520 | 1.00 | 5 |
| 6 | 25.0 | 411–628 | 537 | 1.03[a] | 5 |
| 21 | 25.0 | 524–725 | 632 | 1.21[b] | 5 |
| 33 | 25.0 | 498–603 | 554 | 1.07[a] | 5 |
| 47 | 25.0 | 425–649 | 486 | 0.94[a] | 5 |

[a]Not significantly different from deet at the 0.05% level of confidence.
[b]Significantly different from deet at the 0.05% level of confidence.

TABLE 4

Repellency of compounds applied to the skin as 25% ethanol solutions and compared with deet against deerflies in field tests (Avg. of 5 tests)

| No. | Protection time (min) Range | Adjusted mean | Ratio to deet[a] |
|---|---|---|---|
| 2 | 10–178 | 133 | 3.00 |
| 4 | 4–77 | 23 | 0.51 |
| 6 | 10–173 | 75 | 1.69 |
| 17 | 15–143 | 62 | 1.39 |
| 18 | 6–36 | 40 | 0.89 |
| 20 | 363–421 | 380 | 5.83[b] |
| 21 | 91–203 | 91 | 1.1 |
| 31 | 10–44 | 45 | 0.62 |
| 34 | 20–408 | 141 | 1.8 |
| 35 | 42–182 | 119 | 1.5 |
| 36 | 5–17 | 15 | 0.94 |
| 45 | 4–110 | 18 | 0.24 |
| 47 | 40–160 | 138 | 1.89 |

TABLE 4-continued

Repellency of compounds applied to the skin as 25% ethanol solutions and compared with deet against deerflies in field tests (Avg. of 5 tests)

| No. | Protection time (min) Range | Adjusted mean | Ratio to deet[a] |
|---|---|---|---|
| 49 | 37-244 | 129 | 1.76 |
| 50 | 8-138 | 27 | 1.11 |

[a] Data compiled from a number of tests, accounting for the fluctuation between the protection time and ratio to deet among the members of the series.
[b] Significantly different from deet at the 0.05% level of confidence.

TABLE 5

Repellency of compounds applied to the skin as 25% ethanol solutions and compared with deet against the sandflies *Culicoides mississippiensis* and *Culicoides hollensis* in field tests

| Compounds paired | Average bites/test | Average bites/hour |
|---|---|---|
| *Tests at Yankee Town, Fla. (Avg. 3 tests)* | | |
| Deet | 29.0 | 19.2 |
| 2 | 3.33 | 2.4 |
| Deet | 31.67 | 21.0 |
| 20 | 5.0 | 3.6 |
| Deet | 106.0 | 70.8 |
| 35 | 6.67 | 4.2 |
| Deet | 45.0 | 30.0 |
| 7 | 10.0 | 6.6 |
| Check | 1299 | 865.8 |
| *Tests at Parris Island, S.C. (Avg. 3 tests)* | | |
| Deet | 28.67 | 18.6 |
| 20 | 9.33 | 6.0 |
| Deet | 85.0 | 54.6 |
| 2 | 16.33 | 10.8 |
| Deet | 12.0 | 7.8 |
| 7 | 16.67 | 10.8 |
| Check | 1566 | 1277.4 |

TABLE 6

Repellency of compounds to mosquitoes when applied to the skin as 25% ethanol solutions

| | Ratio to deet | | |
|---|---|---|---|
| | Laboratory test | | Field test |
| No. | Aedes aegypti | Anopheles quadrimaculatus | Aedes taeniorhynchus |
| 2 | 0.22 | 0.28 | 1.5 |
| 4 | 0.22 | 0.11 | 0.77 |
| 6 | 0.14 | 0.74 | 0.82 |
| 7 | 0.70 | 0.11 | 1.15 |
| 17 | 0.24 | 0.33 | 0.52 |
| 18 | 0.13 | 0.05 | 0.07 |
| 19 | 0.20 | 0.73 | 0.44 |
| 20 | 0.68 | 1.0 | 1.4 |
| 21 | 0.64 | 0.86 | 0.7 |
| 31 | 0.24 | 0.08 | 0.45 |
| 33 | 1.12 | 0.86 | 0.69 |
| 34 | 0.89 | 1.0 | 0.34 |
| 45 | 0.23 | 0.11 | 0.12 |
| 47 | 0.28 | 0.24 | 0.99 |
| 49 | 0.55 | 0.09 | 0.65 |

TABLE 7

Repellency of compounds to mosquitoes in tests on cloth.

| | Aedes aegypti | | Anopheles quadrimaculatus | |
|---|---|---|---|---|
| | Days to | | Days to | |
| No. | 1st bite | 5 bites | 1st bite | 5 bites |
| 2 | 15 | 15 | 8 | 8 |
| 4 | 30 | 38 | 38 | 79 |
| 5 | 30 | 38 | 30 | 30 |
| 6 | 106 | 113 | 22 | 38 |
| 7 | 104 | 104 | 111 | 111 |
| 8 | 104 | 104 | 22 | 22 |
| 9 | 52 | 104 | 0 | 22 |
| 10 | 104 | 104 | 1 | 22 |
| 11 | 104 | 104 | 1 | 37 |
| 12 | 15 | 15 | 15 | 15 |
| 13 | 7 | 15 | 7 | 111 |
| 14 | 0 | 1 | 27 | 27 |
| 15 | 15 | 28 | 35 | 35 |
| 17 | 15 | 15 | 15 | 15 |
| 18 | 0 | 30 | 0 | 1 |
| 19 | 28 | 28 | 70 | 94 |
| 20 | 21 | 28 | 28 | 48 |
| 21 | 64 | 87 | 70 | 70 |
| 22 | 69 | 69 | 83 | 83 |
| 23 | 36 | 36 | 36 | 51 |
| 24 | 20 | 20 | 83 | 83 |
| 25 | 83 | 83 | 83 | 83 |
| 26 | 36 | 36 | 36 | 36 |
| 27 | 36 | 36 | 63 | 63 |
| 28 | 28 | 28 | 63 | 83 |
| 29 | 0 | 0 | 35 | 35 |
| 30 | 8 | 8 | 22 | 22 |
| 31 | 15 | 15 | 1 | 1 |
| 33 | 21 | 28 | 28 | 28 |
| 34 | 21 | 28 | 13 | 13 |
| 35 | 28 | 28 | 6 | 6 |
| 36 | 23 | 43 | 0 | 0 |
| 37 | 23 | 51 | 0 | 0 |
| 38 | 36 | 36 | 21 | 21 |
| 39 | 51 | 71 | 0 | 0 |
| 40 | 1 | 23 | 0 | 0 |
| 41 | 8 | 15 | 8 | 8 |
| 42 | 1 | 1 | 36 | 50 |
| 43 | 36 | 77 | 64 | 71 |
| 44 | 28 | 28 | 15 | 15 |
| 45 | 27 | 27 | 1 | 1 |
| 47 | 27 | 27 | 1 | 1 |
| 48 | 33 | 41 | 1 | 1 |
| 49 | 27 | 47 | 1 | 1 |
| 50 | 23 | 51 | 0 | 23 |
| 51 | 36 | 36 | 0 | 21 |
| 52 | 36 | 36 | 8 | 36 |
| 55 | 15 | 15 | 0 | 1 |
| 57 | 8 | 22 | 36 | 105 |
| 58 | 1 | 28 | 22 | 22 |
| 59 | 1 | 35 | 49 | 49 |
| 61 | 34 | 55 | 28 | 28 |
| 62 | 70 | 70 | 70 | 91 |
| 63 | 70 | 128 | 0 | 111 |
| 64 | 70 | 70 | 0 | 76 |
| 65 | 35 | 70 | 0 | 49 |
| 66 | 70 | 70 | 0 | 77 |
| 67 | 21 | 34 | 47 | 47 |
| 68 | 1 | 28 | 20 | 20 |
| 69 | 28 | 28 | 20 | 20 |
| 70 | 28 | 28 | 47 | 47 |
| 71 | 0 | 0 | 47 | 47 |
| 72 | 0 | 34 | 20 | 190 |
| 74 | 0 | 0 | 28 | 28 |
| 76 | 108 | 108 | 21 | 119 |
| 77 | 28 | 108 | 28 | 28 |
| 78 | 21 | 130 | 1 | 8 |
| 79 | 28 | 102 | 0 | 0 |
| 80 | 28 | 102 | 0 | 0 |
| 81 | 28 | 51 | 8 | 8 |
| 82 | 0 | 28 | 8 | 8 |
| 83 | 101 | 108 | 108 | 108 |
| 84 | 8 | 28 | 28 | 28 |
| 85 | 0 | 105 | 134 | 175 |
| 86 | 0 | 1 | 1 | 18 |
| 87 | 0 | 105 | 126 | 126 |
| 88 | 21 | 21 | 24 | 24 |
| 91 | 169 | 169 | 238 | 238 |
| 92 | 29 | 29 | 7 | 182 |
| 93 | 21 | 65 | 21 | 44 |
| 94 | 7 | 21 | 1 | 1 |
| 95 | 7 | 21 | 1 | 126 |

TABLE 7-continued

Repellency of compounds to mosquitoes in tests on cloth.

| | Aedes aegypti | | Anopheles quadrimaculatus | |
|---|---|---|---|---|
| | Days to | | Days to | |
| No. | 1st bite | 5 bites | 1st bite | 5 bites |
| 97 | 0 | 12 | 0 | 12 |
| 98 | 0 | 21 | 126 | 126 |
| 99 | 0 | 12 | 0 | 93 |
| 100 | 7 | 7 | 21 | 268 |
| 101 | 61 | 133 | 238 | 238 |
| 102 | 61 | 93 | 133 | 133 |
| 103 | 42 | 42 | 24 | 54 |
| 106 | 61 | 160 | 160 | 160 |
| 107 | 0 | 36 | 36 | 36 |
| 108 | 22 | 22 | 36 | 134 |
| 110 | 0 | 1 | 36 | 36 |
| 111 | 0 | 0 | 52 | 94 |
| 112 | 13 | 13 | 36 | 104 |
| 113 | 0 | 1 | 134 | 134 |
| 114 | 0 | 36 | 134 | 134 |
| 115 | 0 | 51 | 310 | 318+ |
| 116 | 77 | 134 | 134 | 134 |
| 117 | 22 | 22 | 134 | 134 |

+ Compound still in test.

We claim:

1. A method of repelling stable flies, blackflies, deerflies, sand flies and mosquitoes comprising applying to the skin an effective repellent amount of a compound of the formula

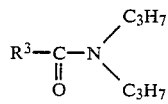

wherein $R^3$ is

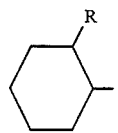

and R is hydrogen.

2. The method of claim 1 wherein the compounds are applied to the skin in an ethanol solution containing from 6.25% to 25%, w/v, of the compound.

* * * * *